United States Patent
Mullins et al.

(10) Patent No.: US 9,498,224 B2
(45) Date of Patent: Nov. 22, 2016

(54) LIGATION BAND DISPENSING CAP ASSEMBLY AND METHODS OF USE

(71) Applicant: Boston Scientific Scimed, Inc., Maple Grove, MN (US)

(72) Inventors: Lindsay Mullins, Cambridge, MA (US); Allison Day, Holden, MA (US); Brad M. Isaacson, Lancaster, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 150 days.

(21) Appl. No.: 14/195,222

(22) Filed: Mar. 3, 2014

(65) Prior Publication Data

US 2014/0249550 A1    Sep. 4, 2014

Related U.S. Application Data

(60) Provisional application No. 61/772,207, filed on Mar. 4, 2013.

(51) Int. Cl.
*A61B 17/10* (2006.01)
*A61B 17/12* (2006.01)
(Continued)

(52) U.S. Cl.
CPC ..... *A61B 17/12013* (2013.01); *A61B 1/00087* (2013.01); *A61B 2017/00296* (2013.01); *A61B 2017/00858* (2013.01); *A61B 2017/00902* (2013.01); *A61B 2017/12018* (2013.01)

(58) Field of Classification Search
CPC ................. A61B 17/12009; A61B 17/12013; A61B 2017/12018; A61B 2017/00818; A61B 17/00234; A61B 17/1285; A61B 17/3205

USPC .......................................... 606/140
See application file for complete search history.

(56) References Cited

U.S. PATENT DOCUMENTS

| 5,624,453 A * | 4/1997 | Ahmed ............ A61B 17/12013 606/139 |
| 5,879,499 A | 3/1999 | Corvi |
| 5,913,865 A | 6/1999 | Fortier et al. |

(Continued)

FOREIGN PATENT DOCUMENTS

| AU | 2003200075 B2 | 4/2003 |
| WO | WO 97/45060 | 12/1997 |

OTHER PUBLICATIONS

International Search Report and Written Opinion for corresponding PCT Application No. PCT/US2014/019876, dated May 27, 2014 (13 pages).

*Primary Examiner* — Katherine M Shi
(74) *Attorney, Agent, or Firm* — Bookoff McAndrews, PLLC

(57) ABSTRACT

A medical device for resecting a tissue. The medical device includes an elongate shaft having a distal end, a proximal end, and a plurality of channels extending therebetween. The medical device also includes a cap assembly disposed at the distal end of the elongate shaft. The cap assembly includes a housing having a proximal portion, a distal portion, and a cavity extending therebetween. The housing is configured to be transparent and includes a friction surface pattern disposed over a portion of an outer surface of the housing. The cap assembly further includes one or more ligation bands disposed on the proximal portion of the housing. The cap assembly also includes a wire interwoven between the ligation bands. The wire is further configured to roll at least one ligation band at a time towards the distal end of the distal portion.

15 Claims, 6 Drawing Sheets

(51) Int. Cl.
  *A61B 1/00* (2006.01)
  *A61B 17/00* (2006.01)

(56) References Cited

U.S. PATENT DOCUMENTS

| | | |
|---|---|---|
| 6,676,672 B2 | 1/2004 | Chu et al. |
| 7,063,709 B2 | 6/2006 | Fortier |
| 8,097,003 B2 | 1/2012 | Hoffman et al. |
| 2005/0143757 A1 | 6/2005 | Ghareeb |
| 2006/0129167 A1 | 6/2006 | Fortier |
| 2007/0265493 A1 | 11/2007 | Zirps et al. |
| 2008/0004622 A1 | 1/2008 | Coe et al. |
| 2008/0091218 A1 | 4/2008 | Richardson |
| 2008/0097478 A1 | 4/2008 | Doughty et al. |
| 2012/0078272 A1 | 3/2012 | Smith |

\* cited by examiner

LIGATION BAND DISPENSING CAP ASSEMBLY AND METHODS OF USE

CROSS-REFERENCE TO RELATED APPLICATIONS

This application claims the benefit of priority from U.S. Provisional Application No. 61/772,207, filed on Mar. 4, 2013, the entirety of which is incorporated by reference herein.

FIELD OF THE DISCLOSURE

This disclosure relates generally to systems and methods for resecting tissue. More particularly, embodiments of the present disclosure relate to systems for endoscopic mucosal resection.

BACKGROUND OF THE DISCLOSURE

A treatment procedure for many gastrointestinal tract problems such as hemorrhoids, mucositis, early gastrointestinal cancer, and varices (vascular and lymphatic malformations) is Ligation Banding, an Endomucosal Resection (EMR) procedure. In this procedure, an elastomeric band is deployed over an undesired tissue such as a dysplastic/metaplastic lesion, a varix, or an internal hemorrhoid. The band exerts a compressive force on the tissue causing it to neck and form a polyp. The polyp may be resected using a snare loop or other resection device.

With conventional technologies, complications may arise. For example, a band can deploy at an angle, placing it over a smaller or larger region than desired. In such instances, the band may fail to compress the tissue properly, either producing a necked polyp, or increasing the risk of perforating the underlying muscular layer. As typically arranged, the bands are stretched over a housing and may require an operator to apply force for deployment. The present disclosure is directed to overcoming the disadvantages mentioned above as well as other problems in the art.

SUMMARY OF THE DISCLOSURE

In one aspect of the disclosure, a cap configured to be disposed at a distal end of an endoscope is disclosed. The cap includes a proximal portion, a distal portion, and a cavity extending between the proximal portion and the distal portions. The proximal portion may be configured to accommodate at least one ligation band on an outer surface thereof. The distal portion may taper towards a distal end of the cap. Further, the distal portion of the cap may have an outer surface configured to facilitate rolling motion of the ligation band thereon.

Another aspect of the disclosure is directed to a medical device. The medical device includes an elongate shaft having a distal end, a proximal end, and a plurality of channels extending there between. The medical device also includes a cap assembly coupled to a distal end of the elongate shaft. The cap assembly further includes a proximal portion, a distal portion, and a cavity extending between the proximal portion and the distal portion thereof. The proximal portion of the cap includes one or more ligation bands disposed over an outer portion of the cap assembly. The distal portion of the cap assembly has an outer surface configured to facilitate rolling of the ligation bands thereon. The cavity of the cap assembly includes a cavity having a region of low pressure to aspirate tissue that is to be resected with the device. In addition, the medical device includes a wire interwoven between the ligation bands. The wire is configured to pull at least one ligation band towards the distal portion of the cap assembly, may be extending through the cavity between the proximal and the distal portion of the cap assembly.

In yet another aspect of the disclosure, a method for resecting tissue is disclosed. The method includes introducing the medical device into a body cavity. The distal portion of the medical device may be positioned proximal to a tissue layer to be resected from a patient's body. The medical device includes an elongate shaft having a distal end, a proximal end, and a plurality of channels extending there between. The medical device also includes a cap assembly coupled to a distal end of the elongate shaft. The cap assembly further includes a proximal portion, a distal portion, and a cavity extending between the proximal portion and the distal portion. The proximal portion of the cap includes one or more ligation bands disposed over an outer portion of the cap assembly. The distal portion of the cap assembly has an outer surface configured to facilitate rolling of the ligation bands thereon. The cavity of the cap assembly includes a cavity for aspirating tissue to be resected by the device. In addition, the medical device includes a wire interwoven between the ligation bands. The wire configured to roll at least one ligation band towards the distal portion of the cap assembly and may extend through the cavity between the proximal and the distal portion of the cap assembly. The method may further include pulling the wire thereby pulling the ligation band. The ligation band may roll over the surface pattern of the cap and may be deployed over the desired tissue.

Additional objects and advantages of the disclosure will be set forth in part in the description which follows, and in part will be apparent from the description, or may become known by practicing the disclosure.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made to embodiments of the present disclosure, an example of which is illustrated in the accompanying drawings. Wherever possible, the same reference numbers will be used throughout the drawings to refer to the same or like parts. The term "distal" refers to the end farthest away from a medical professional when introducing a device in a patient. The term "proximal" refers to the end closest to the medical professional when placing a device in the patient.

Overview

Embodiments of the present disclosure relate to systems and methods for resecting undesired tissue. For example, embodiments of the disclosed device may facilitate removal of deceased dead or other undesired tissue, such as hemorrhoids, mucositis, early gastrointestinal cancer, or varices (vascular and lymphatic malformations), including tissue disposed on, e.g., the mucosal walls of the colon, esophagus, stomach, or duodenum.

In some embodiments, a medical device may include a cap assembly configured for attachment to the distal end of a suitable introduction sheath, such as a catheter shaft, an endoscope, a laparoscope, a colonoscope, an ureterscope, or the like. The cap assembly may include a housing having a proximal portion, a tapering distal portion, and a cavity extending therebetween. The housing may have openings at its proximal and distal ends for allowing communication between the channels of the introduction sheath and the surrounding tissue. One or more ligation bands may be disposed on the proximal portion, and a varying-friction surface pattern may be configured on the surface of the distal portion of the housing. A wire may be interwoven between the ligation bands. The wire may be configured to roll at least one ligation band at a time toward the distal end of the distal portion of the housing.

Exemplary Embodiments

The embodiments disclosed herein are employed along with an endoscopic system, which functions as an introduction mechanism to introduce the disclosed embodiments to a target site within a patient's body. However, it may be noted that the embodiments of the present disclosure may be used along with other introduction devices, sheaths, or systems, such as trocars, catheter sheaths, laparoscopes, colonoscopes, ureterscope, or the like.

Figure 1:
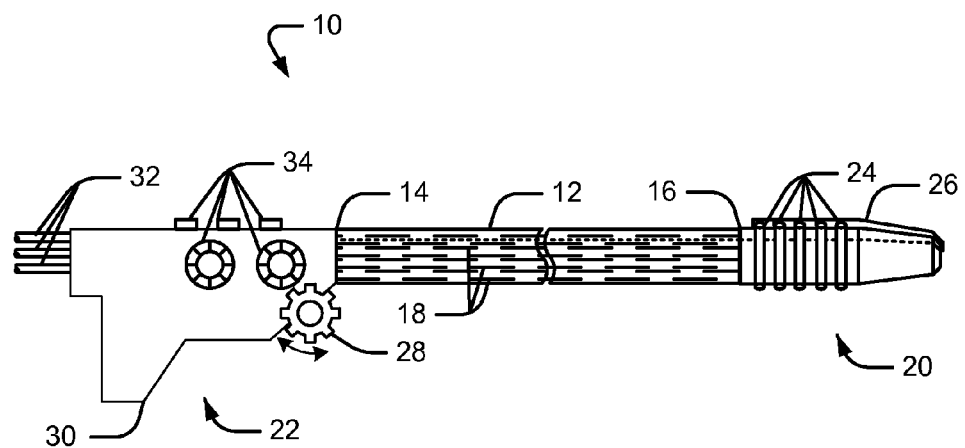
FIG. 1 depicts an exemplary endoscopic system according to an embodiment of the present disclosure.

FIG. 1 depicts an endoscopic system 10. The system 10 includes a catheter shaft 12, a cap assembly 20, and a hub-handle assembly 22. The catheter shaft 12 may have a proximal end 14, a distal end 16, and a plurality of working channels 18 extending through the catheter shaft 12. The channels 18 may carry medical devices such as a vacuum suction mechanism, an endoscopic camera, light source, or the like. The cap assembly 20 is attached to the distal end 16 of catheter shaft 12. One or more ligation bands 24, and a number of such bands, generally 4, 5, 6, or 7 bands, may be disposed over cap assembly 20. It should be appreciated that any number of bands may be disposed over cap assembly 20. As known in the art, ligation bands 24 are resilient, formed of a material such as rubber, and dimensioned to constrict and resect tissue. One or more wires 26 extend from a rotatable knob 28 on the hub-handle assembly 22, through one or more channels 18 in catheter shaft 12, to the cap assembly 20. For example, the one or more wires 26 may be coupled to a pulley (not shown) coupled to the rotatable knob 28, such that rotation of the rotatable knob 28 can rotate the pulley to pull the one or more wires 26. The wires 26 connect to the ligation bands 24 such that one band can be deployed at a time. Details of such a wire mechanism are provided in U.S. Pat. No. 5,913,865, which is expressly incorporated herein by reference in its entirety.

In addition to the rotatable knob 28, the hub-handle assembly 22 includes several additional elements. A handle 30 allows the operator to hold the system 10, and ports 32 permit the introduction of various medical devices into the channels 18. Knobs and other controls 34 such as a steering mechanism and communication and control links to a computer system (none of which are shown) allow the operator to control the endoscopic system 10.

Figure 2:
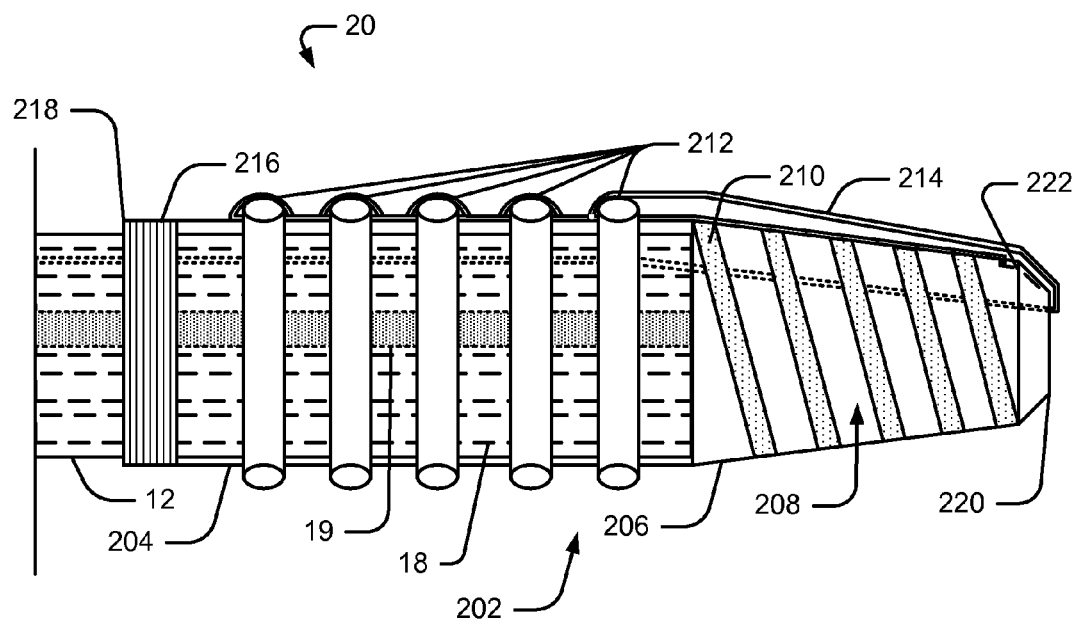
FIG. 2 is a side view of an endoscopic cap assembly for dispensing ligation bands of the exemplary endoscopic system of FIG. 1.

FIG. 2 is a side view of the cap assembly 20. The cap assembly 20 includes a housing 202 attached to the distal end 16 of the catheter shaft 12. The housing 202 includes a proximal portion 204, distal portion 206, and an internal cavity 208. The distal portion 206 carries a varying-friction surface pattern 210, as explained in detail below. In addition, one or more ligation bands 212 are disposed over the proximal portion 204, and a wire 214 interweaves between the ligation bands 212. The tripwire 214 operationally connects to the rotatable knob 28, through the cavity 208 and through one of the channels 18. For example, the tripwire 214 may be coupled to a pulley (not shown) that may rotate with the rotatable knob 28.

The cap assembly 20 may be designed to either permanently or temporarily attach to the distal portion of catheter shaft 12 by an attachment mechanism. Permanent attachment mechanisms may include gluing, welding, soldering or the like, while temporary attachment mechanisms may include a snap-fit, screw-fit, luer-lock, press fit using a silicone component, or similar device formed into the cap assembly 20. In some instances, the cap assembly 20 may be integral to the catheter shaft 12. In an exemplary embodiment, as shown, the cap assembly 20 may have a screw-fit locking mechanism 216 at its proximal end.

The cap assembly 20 may be designed for multiple or a single uses. As a single-use device, for example, the cap assembly 20 may have temporary attachment mechanisms and may be stored in hermetically sealed, sterile packaging before use. A multiple-use device, however, may be sterilizably designed with materials able to withstand high temperature and pressure processing in devices such as an autoclave.

The dimensions of the cap assembly 20 may vary according to the desired application. For example, if cap assembly 20 is anally inserted to resect internal hemorrhoids, the dimensions of the cap assembly 20 may be considerably smaller than a similar device used in connection with treating esophageal varices.

Housing 202 may be a relatively short member (shorter than catheter shaft 12) adapted to cover the distal end 16 of the catheter shaft 12 and facilitate dispensing ligation bands 212. In general, the housing 202 may be a non-pliable, hollow tubular member, with cavity 208 in communication with a proximal opening 218 and a distal opening 220. The proximal opening 218 may join internal channels 18 to the cavity 208.

The proximal opening 218 may be dimensioned to fit over or mate with the catheter shaft 12. In some instances, the cross-sectional shape of the proximal portion 204 may be circular, though other shapes may be employed as needed to be complimentary to the distal end 16 of the catheter shaft 12. In addition, the cross-sectional dimensions of the proximal portion 204 may be uniform or may vary along its length.

The distal portion 206 may be configured with a generally decreasing taper from its proximal end to the distal opening 220 to facilitate dispensing the ligation bands 212. Thus, the distal portion 206 may have a conical, hemispherical, or a funnel-like shape. The distal end of the distal portion 206 may be chamfered to further facilitate deployment of ligation bands 212 over a desired target tissue, and it may be made atraumatic to reduce the likelihood of inadvertent damage to the surrounding tissue. In addition, the distal end of the distal portion 206 may contain slots 222, formed longitudinally in the surface of distal portion 206. The wire 214 may be interwoven between the bands 212 and the slots 222 such that proximally pulling the wire 214 deploys one band 212 at a time.

The housing 202 may be configured to facilitate visualization of the tissue. In some embodiments, all or a portion of the housing 202 may be made from a transparent material. In some embodiments the entire housing 202 may be transparent, while other embodiments may include a transparent window or similar structure. Any of these alternatives allow an operator to view tissue around the housing 202 by way of a visualization device, such as an endoscopic camera 19, carried within one of the channels 18.

Surface pattern 210 is designed to provide a varying-frictional surface to facilitate the bands 212 to roll rather than slide while being dispensed. This characteristic is discussed in detail below. In the illustrated embodiment the surface pattern 210 may take the form of a spiral stripe extending the length of distal portion 206.

Figure 3A:
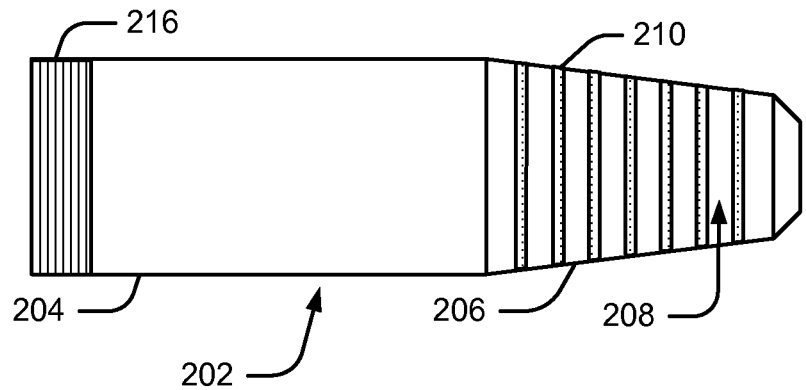
FIGS. 3A, 3B, 3C, 3D, 3E, and 3F illustrate alternate shapes of the surface pattern.
Figure 3B:
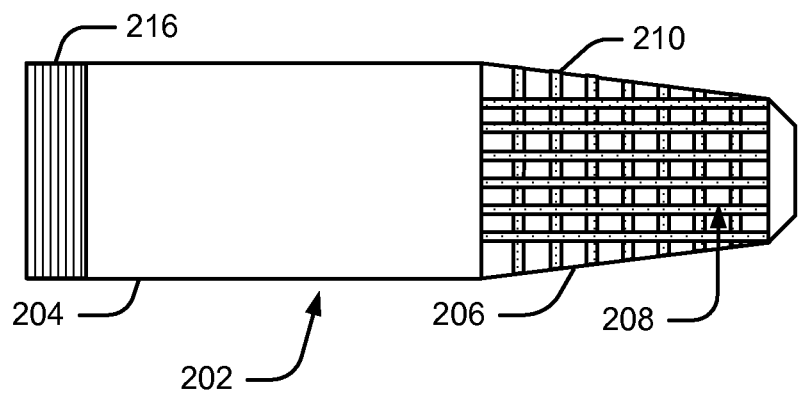
Figure 3C:
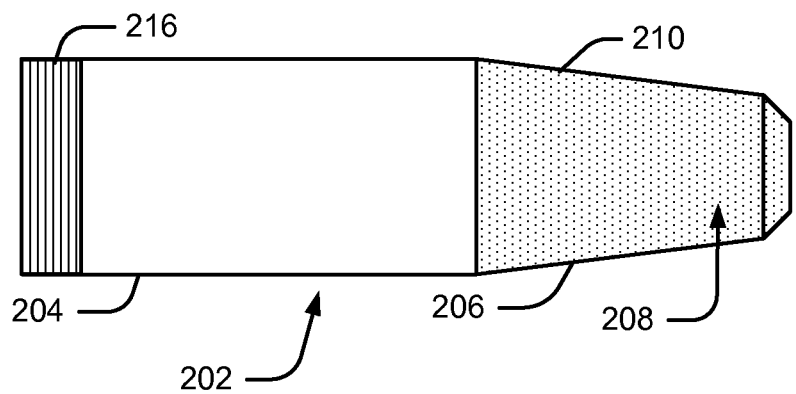
Figure 3D:
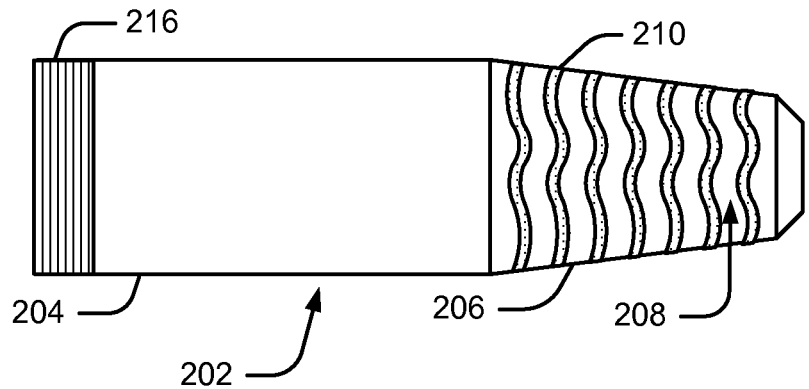
Figure 3E:
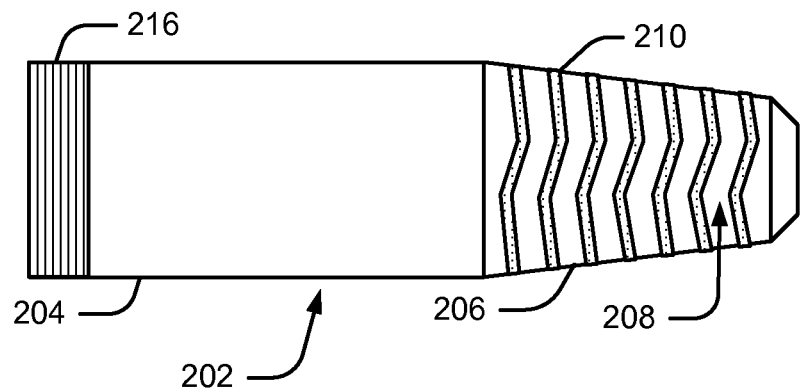
Figure 3F:
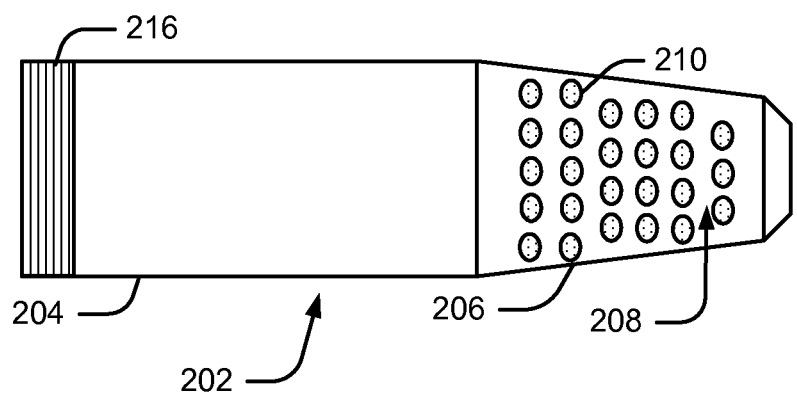

Alternative forms of the surface pattern 210 are shown in FIGS. 3A-3F. FIG. 3A illustrates a set of substantially circular stripes, formed circumferentially and spaced, evenly or irregularly, along distal portion 206. FIG. 3B illustrates a criss-crossed pattern extending over the surface of the distal portion 206. FIG. 3C illustrates a solid pattern extending over the entire outer surface of the distal portion 206. The solid pattern may be formed from a roughened surface having a pattern, regular or irregular, of varying frictional coefficients. FIGS. 3D and 3E illustrate sets of circumferential stripes across the surface of distal portion 206, the stripes being sinusoidal and zig-zag, respectively. FIG. 3F illustrates a pattern of a plurality of patches arranged from the proximal to the distal end of the distal portion 206. Although FIG. 3F shows the patches as substantially oval, it is contemplated that the patches may be of any shape including circular, square, triangular, irregular shape, and/or any other shape.

The surface pattern 210 may be transparent, that is, light can pass through the patterned areas without appreciable scattering, so that objects outside the housing are visible from within, semi-transparent, or translucent, depending upon the materials and techniques used to make the surface pattern 210, described in detail in sections below. In some instances, the surface pattern 210 may be opaque; however in such embodiments, it may occupy a small enough percentage of the total surface area of the distal portion 206 such that it does not substantially obstruct the view of the endoscopic camera 19. The surface pattern 210 may occupy any percentage of the total surface area of the distal portion 206 depending upon its transparency. For example, in some embodiments, a completely transparent surface pattern 210 may occupy 100% of the total surface area of the distal portion 206. In some other embodiments, a translucent or opaque surface pattern 210 may occupy any percentage of the total surface area, including, for example, 25%, 20%, 15%, 10%, or 5% of the total surface area of the distal portion 206.

Returning to FIG. 2, ligation bands 212 may be elastic rubber bands. The ligation bands 212 may be configured to roll over the surface pattern 210. For example, the ligation bands 212 may have a square cross-section, which promotes rolling rather than sliding during deployment. The dimensions and elasticity of the ligation bands 212 may be determined by the desired application of the ligation bands 212. For example, for large lesions, large ligation bands 212 may be needed, whereas for small varices, smaller ligation bands 212 may be used.

Wire 214, as discussed, may be interwoven between the bands 212. The wire 214 may be dimensioned to fit within the channel 18 and may be configured to pull the ligation bands 212 without any undesirable breakage or stretching. Although the present embodiment illustrates a single wire 214, some embodiments may include multiple, wires.

Figure 4:
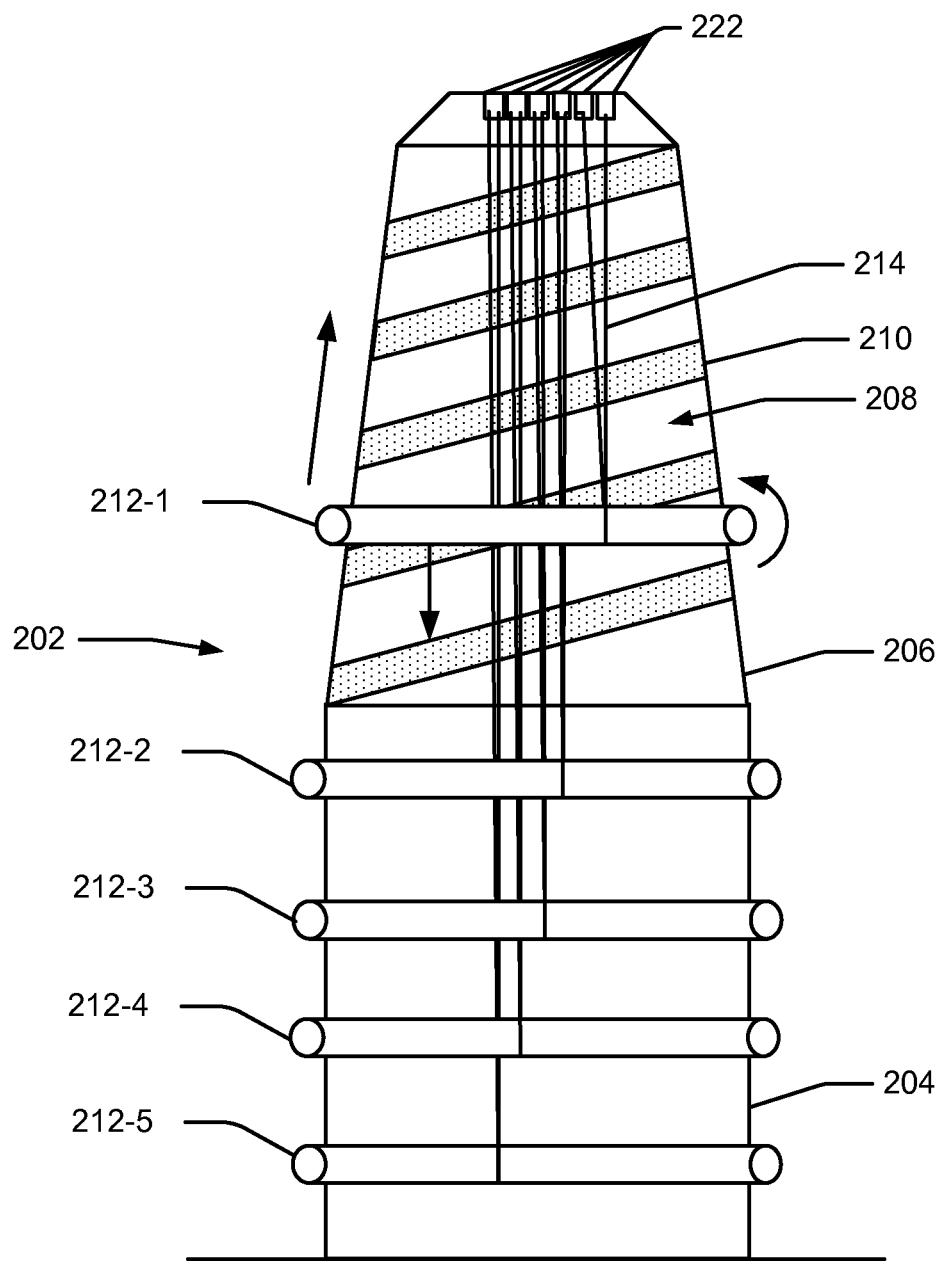
FIG. 4 illustrates operation of the cap assembly of FIG. 2, while dispensing a ligation band.

FIG. 4 illustrates deployment of the ligation bands 212 from housing 202. Ligation bands 212-1-212-5 are arranged on the proximal portion 204. The proximal end of a wire 214 extends distally from rotatable knob 28 (FIG. 1), or a pulley (not shown) coupled to the rotatable knob 28, through distal opening 220, and through one of a number of slots 222. Wire 214 wraps around the first ligation band 212-1, then returns distally to an adjoining one of slots 222, wraps around the edge of that slot, and then extends proximally to the next ligation band 212-2. That pattern continues until each ligation band 212 receives at least one wrap of wire 214, such as a single wrap of wire 214, or alternatively, a double wrap of wire 214.

As the operator pulls the wire 214 proximally, the wire pulls the first ligation band 212-1 which may move from the proximal portion 204 to the distal portion 206 (initially, to the position shown in FIG. 4). When the band 212-1 reaches the distal portion 206, it may experience friction generated by the high-friction surface pattern 210. The frictional force acting on the contacting surface of the ligation band 212-1, acting in collaboration with the force of tension exerted by the wire 214, generates a torque on the band 212-1, and initiates rolling motion of the ligation band 212-1 over the distal portion 206. Specifically, the varying friction surface pattern over the distal portion has a coefficient of friction sufficient to generate a torque to support rolling of the ligation band over the distal portion. This increased frictional force is important when the ligation bands 212 are used in conditions where the bands 212 may be exposed to lubricants, which may be present for minimizing trauma to areas of tissue during intubation, and/or exposed to mucous in the gastrointestinal tract.

A wide range of materials may be used to make the cap assembly 200 and its components. Suitable materials may include metals, polymers, metal-polymer composites, and the like. Some examples of suitable metals and metal alloys include stainless steel, such as 304V, 304L, and 316LV stainless steel; mild steel; nickel-titanium alloy such as linear-elastic and/or super-elastic nitinol, other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include Poly (methyl methacrylate) (PMMA), polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenyleneterephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, polyisoprene, other suitable materials, or mixtures, combinations, copolymers thereof, polymer/metal composites, and the like. These are just examples and should not be seen as limiting.

The housing 202 may be made of one or more suitable polymeric or metallic materials known in the art, for example the materials discussed above. In some implementations, a combination of materials may be employed. For example, the housing 202 may be made of a biocompatible, transparent, non-pliable material that can withstand high static and dynamic pressure exerted by the ligation bands 212 such as Poly(methyl methacrylate) (PMMA), ethylene tetrafluoroethylene (ETFE), polycarbonate, or the like.

The surface pattern 210 may be made by applying a clear, slightly adhesive coating on the regions marked by the surface pattern 210. This coating may allow for visualization using the endoscopic camera 19 in addition to imparting a frictional surface to promote rolling. In some alternative embodiments, the surface pattern 210 may be produced by forming the surface pattern 210 on the housing 202 by abrasion. Sand blasting, etching, or similar processes may be used to abrade the housing 202 surface to give it a roughened finish. The abraded surface pattern 210 may provide sufficient friction to help ensure that ligation bands 212 roll rather than slide.

In some alternative embodiments, a two-shot molding process may be employed. In such embodiments, the surface pattern 210 may be made up of a friction-inducing polymeric material molded as flat strips or patches on the surface of the housing 202. Alternatively, friction inducing metallic coatings may be applied on the housing 202 as the surface pattern 210. For example, a metal or metal alloy powder may be attached to the surface of the housing 202 to form a high-friction surface pattern 210. A person of ordinary skill in the art may contemplate various other techniques and materials to form the surface pattern 210.

In some alternative embodiments, one or more surfaces of the housing 202 may include one or more micropatterns forming the surface pattern 210. The one or more micropatterns may be formed on the one or more surfaces of the housing 202 during a molding process used to form the housing 202. It is also contemplated that the one or more micropatterns may be formed on one or more surfaces of the housing 202 by a material removal process carried out on the one or more surfaces of the housing 202. It is also contemplated that the one or more micropatterns may be added to one or more surfaces of the housing 202 by adding one or more materials to the one or more surfaces of the housing 202. It is also contemplated that the one or more micropatterns may be formed using lithographic patterning methods, such as microlithography, nanolithography, photolithography, and/or any other suitable micropatterning process. A person of ordinary skill in the art may contemplate various other techniques and materials to create the micropatterning.

In some alternative embodiments, the surface pattern 210 may be formed by providing one or more low-friction regions on the housing 202. For example, the housing 202 may be formed at least partially, or in some embodiments entirely, with one or more high-friction regions. The one or more high-friction regions may be formed in any suitable manner, such as by using the above-described methods and processes. Smoothing processes, such as grinding, polishing, and the like, may be carried out on one or more of the high-friction regions, to create one or more low-friction regions. Exemplary low-friction regions are shown between the regions having the surface pattern 210 in FIGS. 2-5C. Less friction is present between the ligation bands 212 and the low-friction regions than between the ligation bands 212 and the high-friction regions. The surface pattern 210 may be a fixed pattern that remains in a fixed position on the cap assembly 20.

The ligation bands 212 may be made of elastic polymeric or rubber materials. The ligation bands 212 may expand/contract over a very wide range of circumferences and may exert a ligating force when contracted. In addition, the ligation bands 212 can maintain the described properties when subjected to storage, and the like. The ligation bands 212 may also be sterilized, and the bands 212 may be capable of maintaining the described properties during any sterilization.

To aid in detecting the position of ligation bands 212 within a patient's body, at least some portions of the ligation bands 212 may include radiopaque materials such as gold, palladium, platinum, tantalum, tungsten alloy, or polymeric materials loaded with radiopaque agents such as barium sulfate ($BaSO_4$) or bismuth sub carbonate ($(BiO)_2CO_3$). Radiopaque materials are capable of producing a relatively bright image on a fluoroscopic monitor or other imaging device.

Ligation bands 212 may be coated with an antibacterial covering to inhibit bacterial growth on their surfaces. The antibiotic coating may contain an inorganic antibiotic agent, disposed in a polymeric matrix that may aid the antibiotic agent to adhere to the surface of the ligation bands 212. A drug-releasing coating may be applied to the ligation bands 212 to assist in delivery of drugs to the severing site.

The bands 212 may have a frictional surface that may increase the friction between the bands 212 and the surface pattern 210, thereby increasing the rotational torque, and hence angular motion of the ligation bands 212. Alternatively, an adhesive coating may be applied on the ligation bands 212 to increase their surface friction along with the surface pattern 210 on the housing 202. Additionally or alternatively, the bands 212 may have a roughened surface finish to improve tissue retention and prevent sloughing off over time.

Figure 5A:
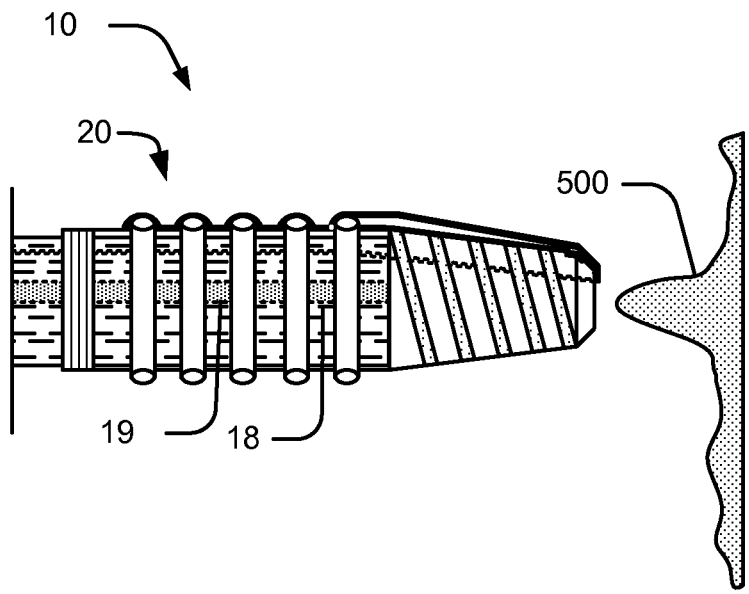
FIGS. 5A, 5B, 5C, and 5D depict an exemplary method of using the exemplary cap assembly of FIG. 2.

FIGS. 5A-5D illustrate use of the cap assembly 20 in performing an EMR ligation. As shown, an operator may introduce the endoscopic system 10 into a patient's body through natural anatomical openings or through incisions. Referring to FIG. 5A, the operator then steers the distal portion of the endoscopic system 10 proximate to the target tissue 500. Visualizing the target tissue 500 through the endoscopic camera 19 placed in one of the channels 18, the operator may place the distal portion 206 of the cap assembly 200 over the undesired tissue, such as a lesion, varix, or internal hemorrhoid.

Figure 5B:
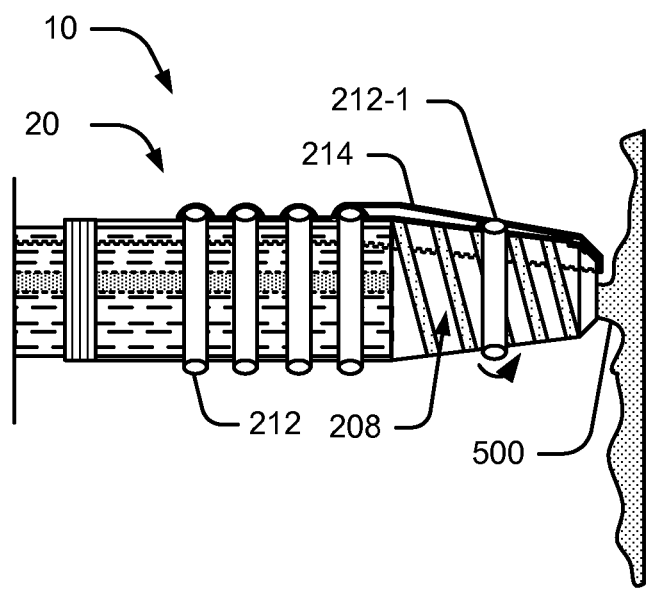

Referring to FIG. 5B, the operator may then use vacuum suction though one of the channels 18 to draw tissue 500 into cavity 208. The operator may draw tissue 500 until the tissue 500 completely blocks the view of the endoscopic camera 19. This condition is conventionally referred to as 'Red Out', and may indicate the maximum amount of tissue 500 that can be accommodated within the cavity 208. In alternative embodiments, a fluid such as gel, saline, hypertonic glucose, indigo carmine, ethylene blue or the like may be injected under the tissue to form a bleb, thereby raising the targeted tissue. In some cases, the polyp may be large and flat and multiple injections may be given around the polyp or directly into the middle of the polyp 500. Next, the operator uses rotatable knob 28 to pull the wire 214. The first ligation band 212-1 may then roll over the tapered distal portion 206 and deploy over the desired tissue 500 causing the tissue to neck and form a banded polyp 500. The band may be in a fully closed position, including the entire targeted tissue.

Figure 5C:
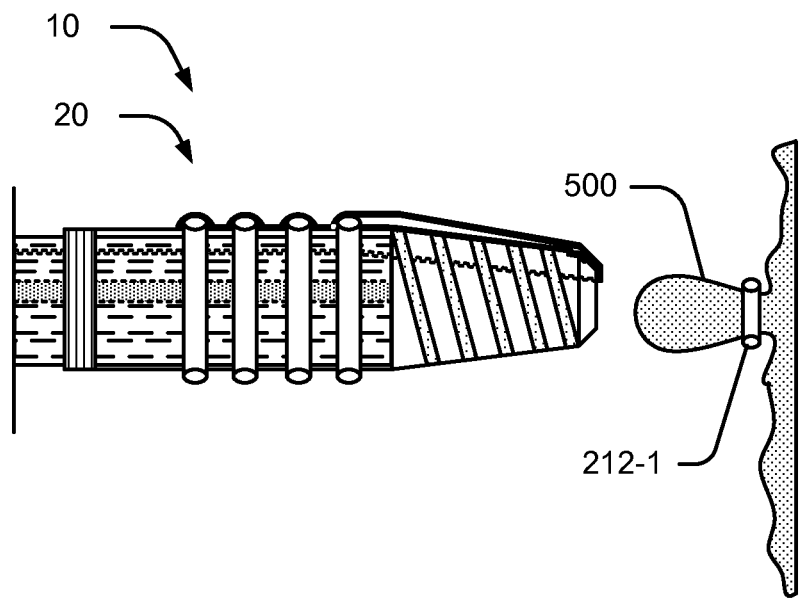
Figure 5D:
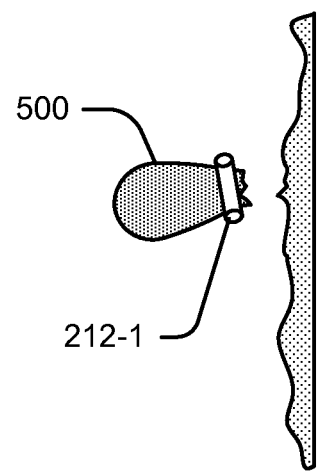

Referring to FIG. 5C, the operator may then stop vacuum suction, and withdraw the cap assembly 200 from the polyp 500. The process can be repeated multiple times until all ligation bands (212-1, 212-2, and 212-3) have been deployed, although only a single deployed band is shown. After ligating the required tissue 500, the operator may choose to resect the polyp 500, using a snare or similar conventional device, as shown in FIG. 5D. The operator may also retract the endoscopic system 10 from the patient's body.

Referring to FIG. 5D, it is also contemplated that blood supply to the tissue 500 may stop because of the compressive force of the band 212-1, which may lead to the eventual death of the tissue 500 in hemostasis applications. The dead tissue 500 may be allowed to fall off naturally, or the operator may choose to resect the tissue 500 immediately, using a snare or similar conventional device, as in the case of removing polyps formed in EMR.

In another embodiment of the present disclosure, the tissue 500 may be a varix, such as one of a plurality of esophageal or anorectal varices, or a hemmorhoid. Varices and hemmorhoids may be removed in the same way that polyps, and tissue in hemostatis applications, are removed, as shown in FIGS. 5A-5D.

Embodiments of the present disclosure may be used in any medical or non-medical procedure. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A medical device configured to be disposed at a distal end of an endoscope, the medical device comprising:
   at least one ligation band;
   a cap, including:
      a proximal portion configured to accommodate the at least one ligation band on an outer surface thereof;
      a distal portion, tapering towards a distal end thereof, the distal portion including an outer surface having a fixed pattern formed thereon, the fixed pattern remaining in a fixed position on the cap, and the fixed pattern having a portion with a first frictional coefficient and a portion with a second frictional coefficient different than the first frictional coefficient, configured to facilitate a rolling motion of the at least one ligation band thereon while the fixed pattern remains in the fixed position, wherein the portion with the first frictional coefficient forms an annular stripe that extends around an entire circumference of the distal portion; and
      a cavity extending between the distal portion and the proximal portion.

2. The medical device of claim 1, wherein the fixed pattern is one of a spiral, a circular, a sinusoidal, a crisscross, and an irregular pattern.

3. The medical device of claim 1, wherein the portion with the first frictional coefficient is a rough surface, having a first coefficient of friction value greater than a second coefficient of friction value of the portion with the second frictional coefficient, the first coefficient of friction value being sufficient to facilitate rolling of the at least one ligation band thereon.

4. A medical device comprising:
   an elongate shaft having a distal end, a proximal end, and a plurality of channels extending therebetween;
   a cap assembly coupled to a distal end of the elongate shaft, the cap assembly having a proximal portion, a distal portion, and a cavity extending between the proximal and distal portions, wherein:
      the proximal portion has one or more ligation bands disposed over an outer portion thereof, and
      the distal portion has an outer surface having a pattern formed thereon, the pattern having a plurality of portions having a first frictional coefficient and a plurality of portions having a second frictional coefficient different than the first frictional coefficient, configured to facilitate rolling of the ligation bands thereon, wherein the plurality of portions having the first frictional coefficient and the plurality of portions having the second frictional coefficient alternate in a proximal-distal direction along the outer surface, and wherein at least one of the plurality of portions having the first frictional coefficient forms a circumferential stripe that extends continuously around a circumference of the distal portion;
   a wire interwoven between the ligation bands and extending through the cavity between the proximal and the distal portion of the cap assembly, the wire being configured to roll at least one ligation band towards the distal portion of the cap assembly.

5. The medical device of claim 4, having a vacuum source coupled to the distal end of the elongate shaft, the vacuum source being configured to maintain a region of low pressure within the cavity of the cap assembly.

6. The medical device of claim 4, wherein the wire is anchored to the distal portion of the cap assembly.

7. The medical device of claim 6, wherein the distal portion has a plurality of slots therein, and the wire is interwoven with the ligation bands in succession, through multiple loops, each loop having a first end anchored to one of the plurality of slots, and a second end coupled to one of the ligation bands.

8. The medical device of claim 7, wherein the wire wraps around a first ligation band, returns distally and wraps around one of the plurality of slots, and extends proximally to a next ligation band.

9. The medical device of claim 4, wherein the distal portion of the cap assembly is tapered, having a continuously decreasing cross-section.

10. The medical device of claim 4, wherein the plurality of portions having the first frictional coefficient and the plurality of portions having the second frictional coefficient each allows light to pass therethrough and into the cavity.

11. The cap of claim 4, wherein the pattern is one of a spiral, a circular, a sinusoidal, a criss-cross, and an irregular pattern.

12. A method for resecting tissue comprising:
introducing a medical device into a body cavity, and positioning a distal portion of the medical device proximal to a tissue layer to be resected from a patient's body, the medical device comprising:
an elongate shaft having a distal end, a proximal end, and a plurality of channels extending therebetween; and
a cap assembly coupled to a distal end of the elongate shaft, the cap assembly having a proximal portion, a distal portion, and a cavity extending between the proximal and distal portions, wherein:
the proximal portion has one or more ligation bands disposed over an outer portion thereof; and
the distal portion has an outer surface having a pattern formed thereon, the pattern having a plurality of portions having a first frictional coefficient and a plurality of portions having a second frictional coefficient different than the first frictional coefficient, configured to facilitate rolling of the ligation bands thereon, wherein the plurality of portions having the first frictional coefficient and the plurality of portions having the second frictional coefficient alternate in a proximal-distal direction along the outer surface, and wherein at least one of the plurality of portions having the first frictional coefficient forms a circumferential stripe that extends around a circumference of the distal portion;
a wire interwoven between the ligation bands, and extending through the cavity between the proximal and the distal portion of the cap assembly, the wire being configured to roll at least one ligation band towards the distal portion of the cap assembly;
aspirating a tissue into the cavity of the housing through a distal opening in the housing; and
deploying a ligation band over the desired tissue.

13. The method of claim 12 comprising resecting the tissue after the ligation band is deployed.

14. The method of claim 12, wherein the tissue is resected by at least one of the snare or the ligation band.

15. The method of claim 12, wherein the circumferential stripe has an arc length about the circumference of the distal portion greater than a width measured in a proximal to distal direction.

* * * * *